(12) United States Patent
Bergström et al.

(10) Patent No.: US 6,566,570 B1
(45) Date of Patent: May 20, 2003

(54) PROCESS FOR PREPARING CYCLIC MONOMERS

(75) Inventors: Christer Bergström, Espoo (FI); Arto Mölsä, Helsinki (FI); Juhana Ruotoistenmäki, Helsinki (FI)

(73) Assignee: Optatech Corporation, Espoo (FI)

( * ) Notice: Subject to any disclaimer, the term of this patent is extended or adjusted under 35 U.S.C. 154(b) by 0 days.

(21) Appl. No.: 09/601,647

(22) PCT Filed: Feb. 5, 1999

(86) PCT No.: PCT/FI99/00084

§ 371 (c)(1),
(2), (4) Date: Aug. 4, 2000

(87) PCT Pub. No.: WO99/40050

PCT Pub. Date: Aug. 12, 1999

(30) Foreign Application Priority Data

Feb. 6, 1998 (FI) .................................................. 980268

(51) Int. Cl.⁷ ............................ C07C 2/76; C07C 13/28; C07C 2/50

(52) U.S. Cl. ...................................... 585/361; 585/360

(58) Field of Search .............................. 585/21, 22, 23, 585/360, 361

(56) References Cited

U.S. PATENT DOCUMENTS

| | | | |
|---|---|---|---|
| 2,966,527 A | 12/1960 | Schmerling | ................. 260/666 |
| 3,660,508 A | 5/1972 | Dart et al. | ................. 260/666 |
| 4,720,715 A | * 1/1988 | Omae et al. | ............. 346/135.1 |

FOREIGN PATENT DOCUMENTS

| | | | |
|---|---|---|---|
| EP | 0 002 278 | 6/1979 | ........... C08G/61/08 |

OTHER PUBLICATIONS

H. Beyer, W. Walter, "Bicyclic Terpenes", *Textbook of Organic Chemistry*, pp. 579–596. Patent translation.
H. R. Christen, *Fundamentals of Organic Chemistry*, pp. 769–770. No English.
Dieter Hellwinkel, *Systematic Nomenclature of Organic Chemistry*, pp. 21 to 29. Not Available.
J. W. Feast et al., "Metathesis Polymerization of 1,7, 7–trimethylbicycloä2.2.lähept–2–en a Well Defined Molybdenum Initiator", J. Mol. Catal., (1994), 90 (1–2), 87–100 (Abstract).
STN International, File CAPLUS, CAPLUS accession No. 1994:436268, Document No.121:36268 Feast, James W. et al.: "Metathesis polymerization of 1, 7, 7–trimethylbicyclo 2.2. lahept–2–en a well defined molybdenum initiator"; & J. Mol. Catal. (1994), 90 (1–2), 87–100.
Methoden der Organischen Chemie, Band V/1b, 1972, pp. 134–142.
Beilsteins Handbuch der Organischen Chemie, 4. Auflage, 5. Band, 1922, pp. 155–156.
Beilsteins Handbuch der Organishen Chemie, 4. Auflage, 1. Erganzungswerk, 5. Band, 1930, pp. 80–81.
Beilsteins Handbuch der Organischen Chemie, 4. Auflage, 2. Erganzungswerk 5. Band, 1943; p. 105.

* cited by examiner

*Primary Examiner*—Thuan D. Dang
(74) *Attorney, Agent, or Firm*—Cohen, Pontani, Lieberman & Pavane

(57) ABSTRACT

A process for producing an unsaturated cyclic compound, comprising the steps of hydrochlorinating a terpene to produce a hydrochlorinated terpene, and subjecting the hydrochlorinate terpene to elimination of hydrogen chloride to form an unsaturated cyclic compound. The terpene is preferably α-pinene, β-pinene, camphene or suitable turpentine fraction. The cyclic compounds can be used as monomers and by means of the invention it is thus possible to produce plastics from renewable raw material sources.

5 Claims, 2 Drawing Sheets

Trimethylnorbornene

Ethylene  Tg = 82 °C
         $n_D$ = 1.513

Propylene Tg = 80 °C
         $n_D$ = 1.511

Norbornene

Ethylene  Tg = 101 °C
         $n_D$ = 1.521

Propylene Tg = 97 °C
         $n_D$ = 1.517

Trimethyl-Tetracyclododecene

Ethylene  Tg = 107 °C
         $n_D$ = 1.521

Propylene Tg = 107 °C
         $n_D$ = 1.519

Tetracyclododecene

Ethylene  Tg = 127 °C
         $n_D$ = 1.528

Propylene Tg = 123 °C
         $n_D$ = 1.525

Trimethylnorbornene

Tg = 45 °C
$n_D$ = 1.529

Norbornene

Tg = 52 °C
$n_D$ = 1.546

Trimethyl-Tetracyclododecene

Tg = 93 °C
$n_D$ = 1.519

Tetracyclododecene

Tg = 110 °C
$n_D$ = 1.527

PROCESS FOR PREPARING CYCLIC MONOMERS

PRIORITY CLAIM

This is a national stage application based on and claiming priority from, PCT/FI 99/00084, filed on Feb. 05, 1999 which in turn claims priority from Finnish Application 980268 filed on Feb. 6, 1998.

BACKGROUND OF THE INVENTION

1. Field of the Invention

The present invention relates to new cyclic olefins. In particular, the invention concerns a process for producing unsaturated cyclic compounds from terpenes. Further, the invention concerns polymers comprising repeating units of the new cyclic olefins.

2. Description of Related Art

Cyclic Olefin Copolymers, COC, are polymeric materials of high interest. They are particularly attractive because their properties can easily be varied and the materials be used in various articles ranging from elastomers to High Perfomance Engineering Plastics. A further advantage of these materials is that they can be made using existing polyethylene or polypropylene polymerization reactors.

The COC's are commercially prepared by copolymerizing, cyclic monomers, such as norbornene or substituted norbornenes, with olefinic comonomers, in particular lower alkenes or styrene. The copolymerization reactions are typically carried out in the presence of catalysts. Thus, tetracyclododecene is copolymerized with ethylene using vanadium-type Ziegler-Natta catalysts (Mitsui Chemical's APEL). Metallocene catalysts have been also used for the copolymerization of norbornene with ethylene (commercially available products are Mitsui Chemical's APO and Ticona's TOPAS). Soft elastomeric types of polyolefins are obtained by Idemitsu Kosan by copolymerization of small amounts of norbornene with ethylene. Furthermore, the use of metallocenes for homopolymerization of norbornene as well as for catalytic copolymerization of substituted norbornenes with ethylene, propylene and styrene is known in the art. Other Single Site Catalysts, like palladium and nickel catalysts, have been used in homo- and copolymerization of norbornene and substituted norbornenes. Engineering types of COC are made by ring-opening methathesis polymerization (ROMP) of substituted norbornenes (commercially available products are represented by BF Goodrich's TELENE OP, Nippon Zeon's ZEONEX and Japan Synthetic Rubber's ARTON). The ROMP-technique can also be employed from manufacturing elastomers (Hüls' VESTENAMER polycyclooctene and Atochem's NORSOREX polynorbornene) as well as RIM thermosets (BF Goodrich's TELENE RIM).

The future of the COC-polymers depends, however, to a high degree on the availability and price of the cyclic monomers. All the cyclic monomers used in the art and presented above are made from raw-materials obtainable from the petrochemical industry and originating in a non-renewable source, i.e. oil. Norbornene and tetracyclododecene are made from dicyclopentadiene and ethylene both of which come from the ethylene cracker. The reaction is carried out by subjecting the feed to a Diels-Alder process which is hazardous. There is only one producer (Atochem) of norbornene and tetracyclododecene in the world and a capacity increase is very unlikely.

In the above cases mixtures of endo- and exo-diastereomers are obtained and the exo/endo ratio has significant effects on the polymerlzation processes and the technical properties of the polymers.

Alternatives to norbornene and tetracyclododecene are urgently needed due to technical reasons as well as the supply situation.

BRIEF SUMMARY OF THE INVENTION

It is an object of the present invention to eliminate the problems of the prior art and to provide a process for synthesizing novel cyclic oletins which can be used as monomers for production of polymers by homo- or copolymerization.

It is another object of the present invention to provide a polymer comprising cyclic olefin units according to the present invention.

It is a further object of the present invention to provide new monomeric compounds.

These and other objects, together with the advantages thereof over known processes, which shall become apparent from the specification which follows, are obtained by the invention.

The present invention is based on using a naturally occuring unsaturated compound as a starting material for the synthesis of cyclic olefins. More particularly, the present invention uses terpenes, a group of unsaturated hydrocarbon compounds, which can be obtained from plans by steam distillation or ether extraction. The cyclic olefins are obtained by subjecting the isolated terpenes or a mixture thereof to a two-step process, in which the terpene(s) is (are) first hydrochlorinated and subjected to isomerization and then the chloride derivative thus obtained is subjected to elimination of hydrogen chloride (dehydrochlorination) to form an unsaturated cyclic compound. This compound can be used as a monomer or comonomer in addition polymerizations using, e.g. Ziegler-Natta, metallocene or other single site coordination catalysts; or it can be subjected to ring-opening polymerizations using methathesis catalysts; or it can be subjected to a Diels-Alder reaction to form a multicyclic monomer. By the latter method a new compound, trimethyl-tetracyclododecene, can be synthetized.

In particular, the process for producing novel cyclic olefins includes a hydrochlorination of a terpene and elimination of hydrogen chloride to form an unsaturated cyclic compound.

The polymers according to the present invention are trimethyl-tetracyclododecene.

Considerable advantages can be obtained by means of the present invention. Thus, plastics can now be made from renewable sources. The monomers of the present invention can replace norbornene and tetracyclododene in many processes and for many applications. They can also be used in combination with norbornene, tetracyclododecene and/or other substituted norbornenes in order to modify the technical properties of polymers.

The various features of novelty which characterize the invention are pointed out with particularity in the claims appended to and forming a part of this specification. For a better understanding of the invention, its operating advantages and specific objects obtained by its use, reference should be had to the accompanying drawings and descriptive matter in which there is illustrated and described a preferred embodiment of the invention.

DETAILED DESCRIPTION OF THE INVENTION

Figure 1A:
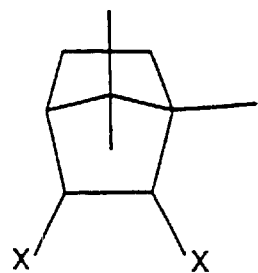
FIGS. 1a to 1d show the monomeric units of trimethyl-norbornene and trimethyl-tetracyclo-dodecene in addition copolymers as compared to corresponding norbornene and tetracyclododecene derived units and it indicates the glass transition points and refractive indices of the various polymers (all copolymers contain 60% of the cyclic monomer)

It is known in the art (cf. A. Streitwieser and C. H. Heathcock: Introduction to Organic Chemistry, Macmillan Publishing Co., 1981) that when treating a terpene with hydrogen chloride the double bond is saturated after which spontaneous rearrangement (isomerization) of the bridgehead and the chlorine occurs.

Based on this general observation, in the present invention reactive cyclic olefins are produced from various isoprenoid compounds, in particular from the volatile $C_{10}$ to $C_{15}$ compounds known as terpenes. These compounds typically contain at least one double bond which will react with hydrogen chloride to yield a chloride adduct. This adduct will spontaneously undergo rearrangement to yield a stable chloride intermediate. By subjecting the chloride intermediate to E2 elimination, hydrogen chloride will be released and an unsaturated cyclic compound obtained.

The invention is particularly useful for transforming the main component of turpentine, α-pinene, as well as β-pinene and camphene to the corresponding norbornene derivative, in particular trimethylnorbornene (bornylene). In addition to isolated compounds, also mixtures of two or more of the afore-mentioned unsaturated compounds can be used. As Example 7 below shows, it is even possible to use natural turpentine or fractions of turpentine as raw material and to effect the hydrochlorination directly on the turpentine.

The reactions of α-pinene, β-pinene and camphene are given in reaction schemes 1–3 below:

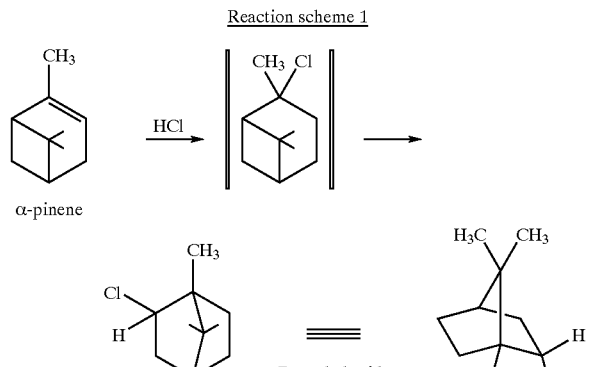

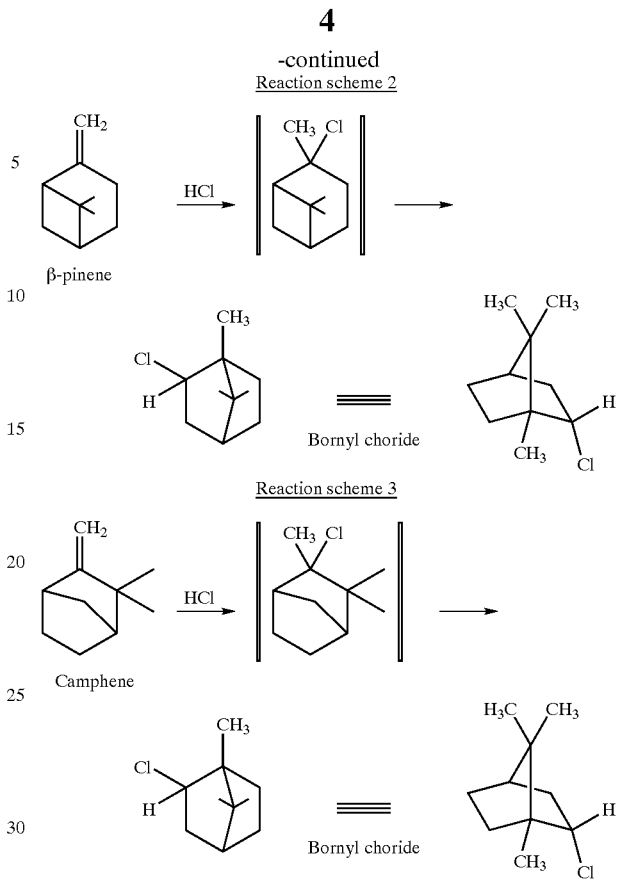

As apparent from the above reaction schemes, hydrogen chloride converts α-pinene, β-pinene and carmphene into bornyl chloride.

Bornyl chloride can be subjected to elimination based on the E2 reaction. The kinetics and mechanism of such elimination is well-known in the art (cf. for example Roberts, J. D. and Caserio, M. C., Basic Principles of Organic Chemistry, 2nd Ed. W. A. Benjamin, Inc. 1997, pp 241–248). The E2 elimination can be effected using a strong base, such as a hydroxide or alkoxide compound. A suitable reagent for this purpose is potassium hydroxide in refluxing ethanol. Because of the equilibrium of the reaction between potassium hydroxide and ethanol the solution is actually a solution of potassium ethoxide in ethanol. Potassium alkoxides and sodium alkoxides are particularly good bases for promoting elimination reactions and potassium t-butoxide in dimethyl sulfoxide, $(CH_3)_3COK$ in DMSO, is especially effective.

Preferably, the conditions have been optimized in order to maximise the exo-diastereomer of the chloride in order to facilitate the elimination reaction.

Reaction scheme 4 indicates the elimination reaction of bornyl chloride.

Reaction scheme 4

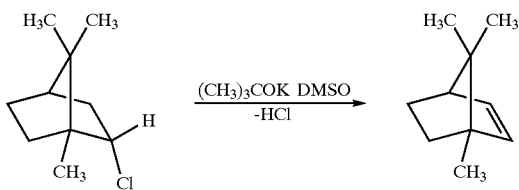

Trimethylnorbornene is a new chemical compound with a double bond without substituents. It is therefore more prone to chemical reactions than the terpenes. It can polymerize in addition polymerization with suitable catalysts as well as in ring opening methathesis polymerization (ROMP). Importantly, it reacts with cyclopentadiene in a Diels-Alder-reaction to form trimethyl-tetracyclododecene. This trimethyl-tetracyclododecene can then be used as a monomer or comonomer in polymerization reactions.

Polymers made from trimethylnorbornene have properties very similar to the corresponding polymers made from norbornene and the properties of polymers made from trimethyl-tetracyclododecene are very similar to the properties of polymers made from tetracyclododecene. The main difference between the polymers is their raw-material source and production process. Trimethylnorbornene and trimethyl-tetracyclododecene are full or partially made from a renewable raw-material source, turpentine obtained from the pine tree, and all the different isomers do not need to be separated when used in the process of the invention.

The particular advantages of producing polymers from the present cyclic monomers or from Diels-Alder reaction products thereof resides in the small density and excellent optical properties of the polymers. Thus, it is possible to prepare polymers which can be characterized as engineering plastics having glass transition temperatures, Tg, above 110° C. It is also possible to manufacture polymer articles having elastomeric properties including a glass transition temperature, Tg, below 10° C. in the final compound.

The polymers can be processed by melt processing methods known per se, e.g., by methods selected from the group of injection moulding, extrusion, blow-moulding, thermoforming and rotational moulding.

Furthermore, bornyl chloride, isobornyl chloride or their mixture can be used as additives in polyolefins in order to improve their barrier properties in the same way as hydrogenated dicyclopentadiene (Hercules).

The following non-limiting examples illustrate the invention in more detail.

EXAMPLE 1

Bornylchloride was made by feeding hydrogen chloride into dried α-pinene. The hydrogen chloride was made by dropping concentrated sulphuric acid onto ammonium chloride which has been wetted by hydrochloric acid. The hydrogen chloride gas was dried by conducting it through a washing bottle containing concentrated sulphuric acid. The reaction flask was kept in ice. The reaction mixture was distilled under vacuum and jelly-like mixture containing 50% bornyl chloride (GC-MS) was obtained.

EXAMPLE 2

Using the jelly-like reaction product of Example 1 the E2-elimination was carried out by dissolving the reaction product in DMSO at 60° C. after which 4.5 equivalents of potassium-tert-butoxide was added. The reaction was allowed to continue under these conditions for 3.5 h. After that the reaction product was made acidic by adding diluted hydrogen chloride and hexane was added in order to get more of the organic phase. The salts and DMSO were eliminated by extracting three times with water in an extraction funnel. The reaction product was separated from the hexane by distilling in vacuum. The white product which was found to contain 70% trimethylnorbornene (GC-MS).

EXAMPLE 3

Bornylchloride was made by feeding hydrochloric gas into dried β-pinene. The hydrochloric gas was made by dropping concentrated sulphuric acid onto ammonium chloride which has been wetted with hydrochloric acid. The hydrogen chloride was dried by leading it through a washing bottle containing concentrated sulphuric acid. The reaction flask was kept in ice. The reaction mixture was distilled under vacuum and a jelly-like mixture containing 62% bornylchloride (GC-MS) was obtained.

EXAMPLE 4

Using the jelly-like reaction product of Example 1 the E2-elimination was carried out by dissolving the product in DMSO at 60° C. after which 4.5 equivalents of potassium-tert-butoxide was added. The reaction was allowed to continue under these conditions for 3.5 h. After that the reaction product was made acidic by adding diluted hydrochloric acid and hexane was added in order to get more of the organic phase. The salts and DMSO were eliminated by extracting three times with water in an extraction funnel. The reaction product was separated from the hexane by distilling in vacuum. A white product was obtained which was found to contain 87% trimethylnorbornene (GC-MS).

EXAMPLE 5

Bornylchloride was prepared by feeding hydrochloric gas into dried camphene. The hydrogen chloride was made by dropping concentrated sulphuric acid onto ammonium chloride which has been wetted by hydrochloric acid. The hydrogen chloride was dried by leading it through a washing bottle containing concentrated sulphuric acid. The reaction flask was kept in ice. The reaction mixture was distilled under vacuum and a white reaction product containing 73% bornylchloride (GC-MS) was obtained.

EXAMPLE 6

Using the reaction product of Example 5 the E2-elimination was performed by dissolving the product in DMSO at 60° C. after which 4.5 equivalents of potassium-tert-butoxide was added. The reaction was allowed to continue under these conditions for 3.5 h. After that the reaction product was made acidic by adding diluted hydrochloric acid and hexane was added in order to get more of the organic phase. The salts and DMSO were eliminated by extracting three times with water in an extraction funnel. The reaction product was separated from the hexane by distilling in vacuum. The obtained white product was found to contain 78% trimethylnorbornene (GC-MS).

EXAMPLE 7

Bornylchloride was made by feeding hydrochloric gas into natural turpentine. Main components of the turpentine were α-pinene, β-pinene, $\Delta^3$-carene, limonene, and terpinolene. The hydrogen chloride was made by dropping concentrated sulphuric acid onto ammonium chloride which has been wetted by hydrochloric acid. The hydrogen chloride was dried by leading it through a washing bottle containing concentrated sulphuric acid. The reaction flask was kept in ice. The reaction mixture was distilled under vacuum and a brownish liquid containing 19% bornylchloride (GC-MS) was obtained.

EXAMPLE 8

Using the Quantitative Structure Property Relationship (QSPR) technique developed by J. Bicerano et al. at Dow Chemical Company polymers made from trimethylnorbornene and trimethyl-tetracyclododecene were simulated and compared with the commercially available norbornene and tetracyclododecene respectively. This topological QSPR method is included in the Molecular Simulations Polymer software package as a separate module named Synthia.

Figure 1B:
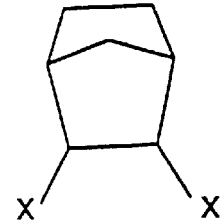
Figure 1C:
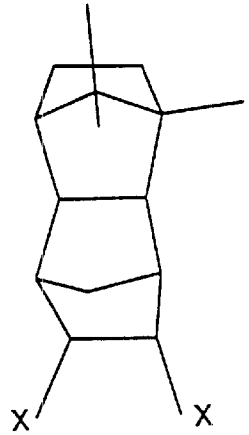
Figure 1D:
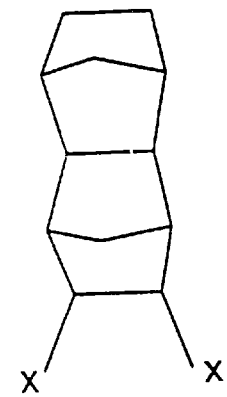

Addition copolymerization (using e.g. metallocene, vanadium type Ziegler-Nata, nickel or palladium type catalysts) with ethylene and propylene are presented in FIG. 1 and the (glass transition temperatures (Tg) and refractive indices for 60 mol-% comonomer incorporation are indicated.

Figure 2A:
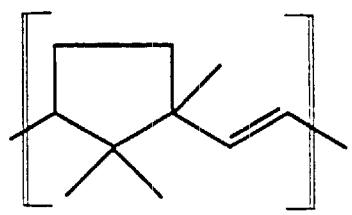
FIGS. 2a to 2d show the monomeric units of trimethylnorbornene and trimethyl-tetracyclo-dodecene in ROMP homopolymers as compared to corresponding norbornene and tetracyclododecene based homopolymers and it indicates the glass transition points and refractive indices of the various polymers.
Figure 2B:
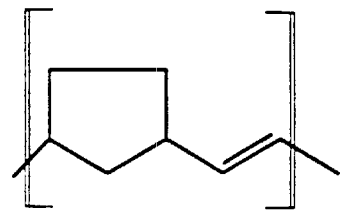
Figure 2C:
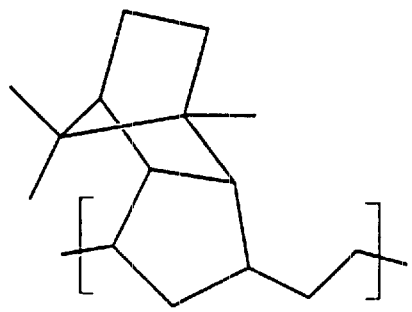
Figure 2D:
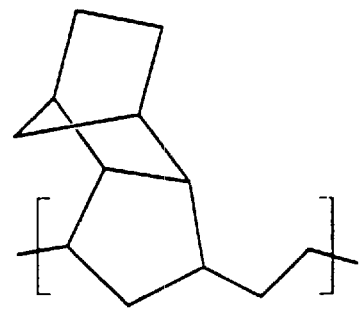

Ring-opening Methathesis Polymerization (ROMP) of homopolymers are presented in FIG. 2 and for the elastomeric type polynorbornene and poly(1,7,7-trimethylnorbornene) the glass transition temperatures (Tg) and the refractive indices are indicated. The ROMP-homopolymers of the corresponding Diels-Alder adducts cyclopentadiene have been hydrogenated, which is the practice when making commercial engineering type ROMP-polymers, in order to decrease the sensitivity to thermal, oxidative and UV-degradation. Also these ROMP-polymers are presented in FIG. 2 and their glass transition temperatures (Tg) and refractive indices are presented.

It is seen that trimethylnorbornene and trimethyl-tetracyclododecene can replace norbornene and tetracyclododecene, respectively, which are short in supply. By using, the cyclic monomers of the present invention also polymers with lower density are obtained and the raw-materials come from renewable sources which are in abundant supply.

From molecular modeling it appears that, when using trimethyl-norbornene or trimethyl-tetracyclododecene as monomers, homopolymers or copolymers with ethylene or propylene with high Tg can be obtained and that in the copolymers Tg increases with increasing incorporation of the cyclic monomer. It can also be noticed that the Tg level is somewhat lower for trimethylnorbornene and trimethyl-tetracyclododecene than for the references but the refractive indices are lower which is an advantage in optical memory media etc. Another advantage is their lower density. By using, the tetracyclic monomers instead of the bicyclic monomers hitcher Tg:s are obtained. Now the refractive indices increase a little for the addition copolymers but decrease for the ROMP-homopolymers. By copolymerizing with propylene somewhat lower Tg:s and refractive indices are obtained compared to ethylene but the reactivities of propylene and the cyclic monomers are more in balance so that higher incorporations of cyclic monomer are possible.

It should be emphasized that the above data on the properties has been obtained by molecular modeling, and it is useful for comparing the properties of various polymers not for determining absolute values. The Tg:s obtained in practical measurements are considerably higher, especially for the addition copolymers. The catalyst systems and the copolymerization conditions also have a significant influence on Tg. Even within one specific catalyst system like the metallocene/MAO-system one can for the same monomer type and incorporation obtain very different Tg:s. This is due to different sequences (random, alternating, block), different enchantments, different diastereomers etc. Therefore the Tg:s obtained from molecular modeling only show the potentials of the cyclic monomers. The refractive indices, however, are more in line with practical measurements (1.51 for ARTON, 1.53 for Zeonex and TOPAS and 1.54 for APO) and, what is more important, they are all considerably lower than for polycarbonate (1.59). In the case of ROMP-elastomers poly-trimethylnorbornene has a lower Tg than poly-norbornene (Norsorex) and can due to the unsaturation be vulcanized to a very soft rubber. Here the refractive indices have no practical significance.

The terms and expressions which have been employed are used as terms of description and not of limitation, and there is no intention in the use of such terms and expressions of excluding any equivalent of the features shown and described or portions thereof, it being recognized that various modifications are possible within the scope of the invention.

What is claimed is:

1. A process for producing 1,7,7-trimethy-norbornene, comprising:
   a) hydrochlorinating a terpene to produce a hydrochlorinated terpene, and
   b) subjecting the hydrochlorinated terpene to an E2-elimination of hydrogen chloride to form 1,7,7-trimethyl-norbornene.

2. The process of claim 1, wherein the terpene is a α-pinene, β-pinene, camphene or a suitable turpentine fraction.

3. The process of claim 1, wherein the E2-elimination is performed using an alkaline compound.

4. The process of claim 3, wherein the alkaline compound is potassium-tert.-butoxide.

5. The process of claim 1, wherein the 1,7,7-trimethyl-norbornene is reacted with cyclopentadiene to form a Diels-Alder adduct.

* * * * *